United States Patent [19]

Zuzich et al.

[11] Patent Number: 5,371,243
[45] Date of Patent: Dec. 6, 1994

[54] POLYETHERCYCLICPOLYOLS FROM EPIHALOHYDRINS, POLYHYDRIC ALCOHOLS, AND METAL HYDROXIDES

[75] Inventors: Anne H. Zuzich; George C. Blytas; Harry Frank, all of Houston, Tex.

[73] Assignee: Shell Oil Company, Houston, Tex.

[21] Appl. No.: 91,466

[22] Filed: Jul. 13, 1993

Related U.S. Application Data

[63] Continuation of Ser. No. 959,953, Oct. 13, 1992, abandoned.

[51] Int. Cl.$^5$ .............................. C07D 319/12
[52] U.S. Cl. .................................. 549/378
[58] Field of Search ........................... 549/378

[56] References Cited

U.S. PATENT DOCUMENTS

| | | |
|---|---|---|
| 2,062,404 | 12/1936 | Dreyfus . |
| 2,487,208 | 11/1949 | Alsop . |
| 3,300,415 | 1/1967 | Ward . |
| 3,425,960 | 2/1969 | Sandler et al. . |
| 3,499,491 | 3/1970 | Wyant et al. . |
| 3,548,010 | 12/1970 | Yoshino et al. . |
| 3,637,774 | 1/1972 | Babayan et al. . |
| 3,968,169 | 7/1976 | Seiden et al. . |
| 4,802,998 | 2/1989 | Mueller et al. . |
| 5,058,679 | 11/1991 | Hale et al. . |
| 5,072,794 | 12/1991 | Hale et al. . |
| 5,076,364 | 12/1991 | Hale et al. . |
| 5,076,373 | 12/1991 | Hale et al. . |
| 5,083,622 | 1/1992 | Hale et al. . |
| 5,085,282 | 2/1992 | Hale et al. . |
| 5,198,416 | 3/1993 | Hale et al. . |
| 5,198,532 | 3/1993 | Blytas et al. . |
| 5,204,444 | 4/1993 | Frank et al. . |
| 5,233,055 | 8/1993 | Blytas et al. . |

FOREIGN PATENT DOCUMENTS

| | | |
|---|---|---|
| 374671A | 12/1988 | European Pat. Off. . |
| 399270A1 | 5/1989 | European Pat. Off. . |
| 324887A | 7/1989 | European Pat. Off. . |
| 333984A | 9/1989 | European Pat. Off. . |
| 374672A | 6/1990 | European Pat. Off. . |
| 382070A | 8/1990 | European Pat. Off. . |
| 382071A | 8/1990 | European Pat. Off. . |
| 386636A | 9/1990 | European Pat. Off. . |
| 386638A | 9/1990 | European Pat. Off. . |
| 391251A | 10/1990 | European Pat. Off. . |
| 391252A | 10/1990 | European Pat. Off. . |
| 398112A | 11/1990 | European Pat. Off. . |
| 398113A | 11/1990 | European Pat. Off. . |
| 3346097A | 7/1985 | Germany . |
| 3842692A | 6/1990 | Germany . |
| 3842703A | 6/1990 | Germany . |
| 3916550A | 11/1990 | Germany . |
| 43-19028 | 8/1968 | Japan . |
| 44-26672 | 11/1969 | Japan . |
| 45-21948R | 7/1970 | Japan . |
| 58-198429A | 11/1983 | Japan . |
| 61-043627A | 3/1986 | Japan . |
| 61-140534A | 6/1986 | Japan . |
| 61-238749A | 10/1986 | Japan . |
| 2216573A | 10/1989 | United Kingdom . |
| 2216574A | 10/1989 | United Kingdom . |
| 2223255A | 4/1990 | United Kingdom . |

*Primary Examiner*—Nicky Chan

[57] ABSTRACT

Method for preparing polyethercyclicpolyol by heating a reaction mixture of an alkali or alkaline earth metal hydroxide with a polyol, adding epihalohydrin to initiate an addition reaction, and heating the mixture until the reaction is complete.

10 Claims, 6 Drawing Sheets

POLYETHERCYCLICPOLYOLS FROM EPIHALOHYDRINS, POLYHYDRIC ALCOHOLS, AND METAL HYDROXIDES

This is a continuation of application Ser. No. 959,953, filed Oct. 13,1992, now abandoned.

BACKGROUND OF THE INVENTION

1. Field of the Invention

This invention relates to polyethercyclicpolyols having high molecular weights and to the preparation thereof. In particular, the invention relates to the preparation of polyethercyclicpolyols which, due to improved molecular properties and characteristics, permit the preparation of improved drilling fluids.

2. Description of the Prior Art

Water-based drilling fluids of the prior art comprise water, clays or polymers, and various drilling fluid additives which control the physical, chemical and/or rheological properties of drilling fluids in wellboxes. It is desirable that such drilling fluids additives inhibit formation of gas hydrates, prevent shale dispersion, reduce swelling of the formation to improve wellbore stability, reduce fluid loss, and reduce filter cake thickness. In order to perform these functions as drilling fluid additives, it is theorized, although the present invention is not limited to this theory, that an ideal polymeric drilling fluid additive would contain large water soluble molecules and have relatively limited crosslinking in spite of high molecular weight. It is difficult to produce polymeric molecules of this the of high molecular weight which do not have extensive crosslinking, and the prior art has been unsuccessful in producing such an ideal drilling fluid additive which performs the desired functions. Accordingly, the present invention provides a process which overcomes these and other problems in the art as more particularly disclosed hereinafter, and which produces polyethercyclicpolyols of significantly improved characteristics as drilling fluid additives.

SUMMARY OF THE INVENTION

The purpose of the present invention is to form polyethercyclicpolycls by an addition reaction between an epihalohydrin and a polyol. This purpose is achieved by reacting an epihalohydrin, an alkali and/or alkaline earth metal hydroxide, and a reactant selected from the group consisting of (a) a polyol having at least two hydroxyl groups, (b) precursors of the polyol, (c) cyclic derivatives of the polyol, and (d) mixtures thereof, wherein the said polyol reactant and the metal hydroxide are first mixed and heated, the epihalohydrin is added to the mixture, and heating of the mixture is continued until the reaction is complete. In another embodiment, the polyol reactant and the metal hydroxide are first mixed with a solvent and heated, the epihalohydrin is added to the mixture, and heating of the mixture is continued until reaction is complete. In yet another embodiment of the invention, the polyol reactant and the metal hydroxide are first mixed and heated, the epihalohydrin is added to the mixture, water is removed from the mixture, and heating of the mixture is continued until the reaction is complete. In an additional embodiment of the invention, the polyol reactant and the metal hydroxide are first mixed and heated and water is removed from the mixture, the epihalohydrin is added to the mixture, and heating of the mixture is continued until the reaction is complete. In still another embodiment of the invention, the polyol reactant and the metal hydroxide are first mixed and heated, the epihalohydrin is added to the mixture, and heating of the mixture is continued until the reaction is complete, after which an alkali and/or alkaline earth metal halide salt byproduct is removed from the mixture by the addition of a lower alkanol to the mixture to precipitate salt, followed by filtration or centrifugation of the mixture.

DESCRIPTION OF PREFERRED EMBODIMENTS

Polyethercyclicpolyols

Figure 1A:
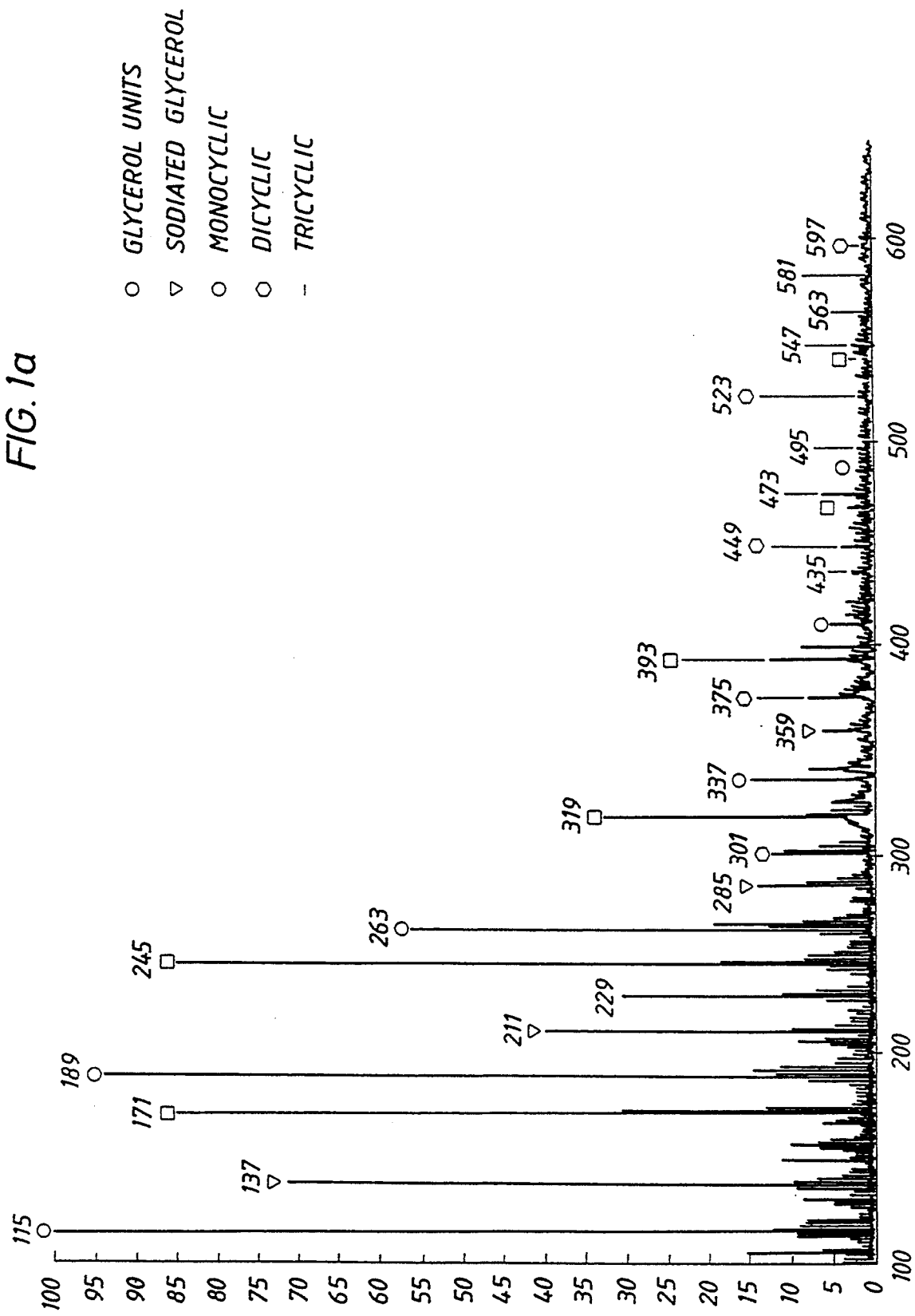
FIGS. 1A–1C disclose fast atom bombardment mass spectroimetry for various samples.

Polyethercyclicpolyols are those having at least 6 carbon atoms, at least 2 hydroxyl groups, and at least 2 ether linkages, but no more than 1800 carbon atoms, 450 hydroxyl groups, and 600 ether linkages. More preferably, polyethercyclicpolyols are those having at least 15 carbon atoms, 5 ether linkages, and at least 5 hydroxyl groups. Most preferably, polyethercyclicpolyols are those having at least 18 carbon atoms, at least 6 hydroxyl groups, and at least 6 ether linkages, but preferably no more than 1200 carbon atoms, 300 hydroxyl groups, and 400 ether linkages. Weight average molecular weights, $M_w$ (vide infra), preferably range from 50,000 to 200,000. Hereinafter "poly" is used to mean two or more, "mono" is used to mean one, "cyclic" is used to mean one or more ring structures, "ether" is used to mean one or more ether linkages, and polyethercyclicpolyol may also be called PECP or polycyclicpolyetherpolyol.

The preparation of polyethercyclicpolyols via the thermal condensation of polyhydric alcohols has been described in patent applications Ser. Nos. 672,200; 672,199; 672,201; 672,198; 672,203 and 672,202 filed Mar. 19, 1991. In these patent applications, it is disclosed that polyethercyclicpolyols may be prepared by the polycondensation of polyhydric alcohol compounds (vide infra), such as glycerol, telomers of glycerol, such as di-, tri-, tetra-, penta-, and hexaglycerols, mixtures of glycerol and its telomers, precursors of trihydric alcohols, such as glycidol, and derivatives of polyhydric alcohols, such as the bis(hydroxymethyl)-p-dioxanes (vide infra), in chemical processes which are accompanied by significant expulsion of water molecules from the polymerizing compounds. The number of ether linkages equals the number of water molecules expelled. For example, Structure (I) is the lowest molecular weight structure containing two glycerol units.

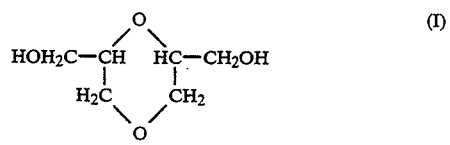

It is formed by condensing 2 glycerol units, expelling two molecules of water. Alternatively, Structure (I) may be formed by the self-condensation of diglycerol, expelling one molecule of water. Structure (I) may be called 2,6-bis(hydroxymethyl)-p-dioxane, or the cyclic dimer of glycerol. Similarly, condensing two Structure (I) units yields Structure (II), containing two terminal hydroxyl groups and five ether linkages.

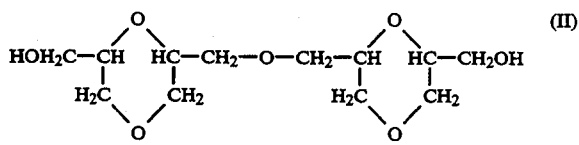
(II)

Structure (II) may also be formed by condensation of four glycerol units with the expulsion of five water molecules. This structure is a dicyclic- poly (or penta) etherdiol, and may be called di-bis(hydroxymethyl)-p-dioxane. Polyethercyclicpolyols may also be formed by further condensation or polycondensation of Structure (II) with itself, or with itself and with polyhydric, at least trihydric monomers, such as glycerol monomers. Dimerization of Structure (II) with expulsion of one molecule of water yields Structure (III).

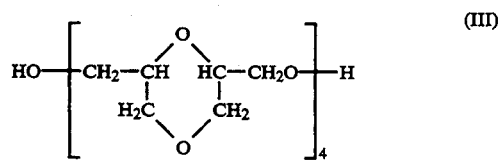
(III)

Copolycondensation of four Structure (I) units with itself and with one glycerol molecule can yield Structure (IV) and its isomeric equivalents.

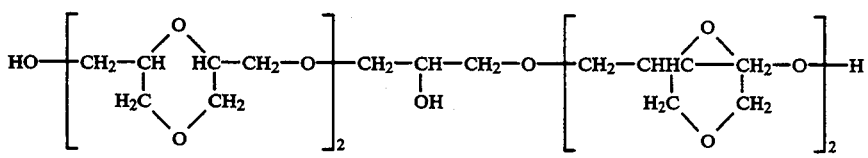

Structure (IV) contains twelve ether linkages, three hydroxyl groups, and four six-membered cyclic diethers, and is formed by the polycondensation of nine glycerol molecules with the expulsion of twelve water molecules. The cyclic diether units and the polycondensed glycerol units, or other polyhydric units, occur randomly in the structure. Disregarding the order of occurrence, a general chemical composition formula representative of all these structures is given by Structure (V).

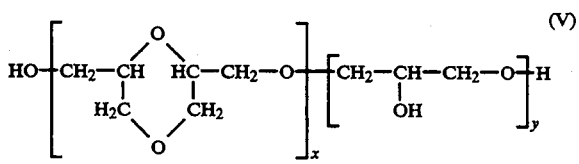
(V)

where x>1 and y>0.

In the present case it is disclosed that polyethercyclicpolyols with the same chemical structures may also be prepared via a novel synthetic route consisting of the addition of epihalohydrins to polyhydric alcohol compounds (vide infra) (such as glycerol, telomers of glycerol, such as di-, tri-, tetra-, penta- and hexaglycerol, and derivatives of polyols, such as the bis(hydroxymethyl)-p-dioxanes) in the presence of stoichiometric amounts of alkali and/or alkaline earth metal hydroxide in a one-step process.

It is theorized, although the invention is not limited to this theory, that this process is composed of a three chemical step reaction cycle: addition, followed by dehydrohalogenation, followed by addition, in which a molecule containing an epoxy functionality reacts with a molecule containing a hydroxyl functionality to yield a molecule containing a hydroxyl group attached to a carbon in the alpha position to another carbon which is bound to a halide atom. Such a molecule may be called a halohydrin. The halohydrin may then react with a metal hydroxide in a dehydrochlorination reaction to yield a molecule with an epoxy functionality, along with metal halide salt and water as byproducts. The new product molecule with the epoxy functionality may then undergo a further addition reaction to another molecule containing a hydroxyl group. Repetitions of this cycle in which di- or polyfunctional product molecules containing one or more hydroxyl groups react with additional epihalohydrin reactant may form molecules of high molecular weight. As a non-limiting, illustrative example of this reaction sequence, epichlorohydrin may react with glycerol to produce a chlorohydrin compound, Structure (VI), containing an ether linkage and a terminal hydroxyl group in Equation (1).

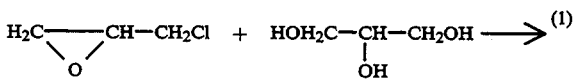
(1)

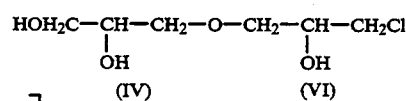
(IV)　　(VI)

The chlorohydrin (VI) may react with sodium hydroxide to produce a glycidyl ether, Structure (VII), as shown in Equation (2). Sodium chloride and water are byproducts of the reaction.

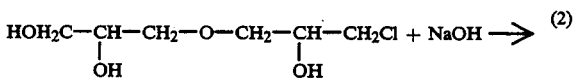
(2)

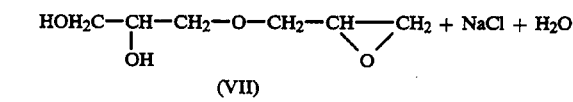
(VII)

The glycidyl ether (VII) may then react with another molecule of glycerol to produce a larger molecule with two ether linkages and two terminal hydroxyl groups, Structure (VIII), in Equation (3).

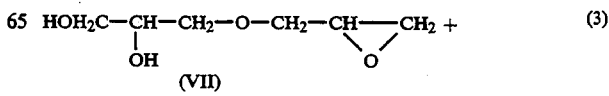
(3)
(VII)

-continued

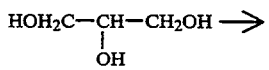

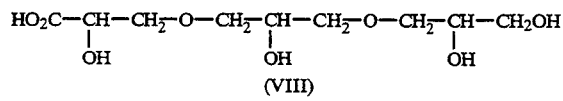
(VIII)

In general, any polyhydric alcohol (vide infra) may substitute for glycerol in Equations (1)–(3). Thus, since glycerol and other polyhydric alcohols are multi-functional, polymeric ethers may be formed by repeating the three step chemical reaction sequence shown in Equations (1)–(3), since the reaction product contains two terminal hydroxyl functionalities and thus may substitute for the polyhydric alcohol monomer in Equation (1).

Theoretically, the molar ratio of polyhydric alcohol monomer to epihalohydrin for a linear chain of infinite length approaches one. However, other reactions may occur simultaneously in the mixture. For example, crosslinking or branching in the product polyethercyclicpolyol may occur by reacting the non-terminal hydroxyl groups on the polyhydric alcohol. It is theorized, although the invention is not limited to this theory, that the non-terminal (internal, or secondary or tertiary) hydroxyls, react less readily with the epoxy group than the terminal (or primary) hydroxyls. Further, it may be possible to control the relative amount of crosslinking by varying the reaction parameters (vide infra).

Still other reactions may also occur in the mixture. In particular, hydrolysis may occur, as shown for Structure (VII) in Equation (4).

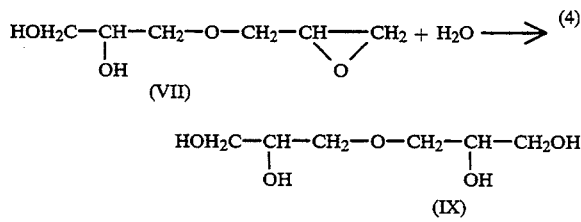

The product, Structure (IX), contains two terminal hydroxyls and no epoxy functionality. In general, increasing amounts of water in the reaction mixture lead to increased occurrence of hydrolysis, and thus a lower molecular weight product is obtained. However, the hydrolysis of epihalohydrin, followed by dehydrohalogenation, is theorized to be an important reaction for the production of the intermediate which is the source of the cyclic ether building unit or monomer of polyethercyclicpolyol, although the invention is not limited to this theory. These reactions are illustrated for the hydrolysis of epichlorohydrin to glycidol in Equations (5) and (6).

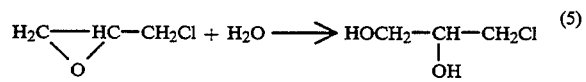

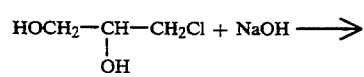

-continued

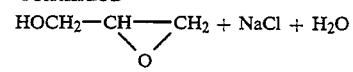

Glycidol may dimerize to produce the cyclic ethers which are called bis(hydroxymethyl)-p-dioxanes, shown in Equation (7). Such cyclic ether units are thought to be essential for the good performance of polyethercyclicpolyols as drilling fluid additives.

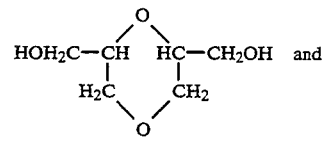 and

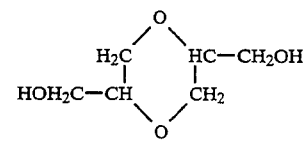

These cyclic ether units each contain two terminal hydroxyl groups, and thus may enter into addition reactions with epoxy functionalities on other molecules, thus incorporating the cyclic diether rings into the polyethercyclicpolyol product, as shown in Equation (8).

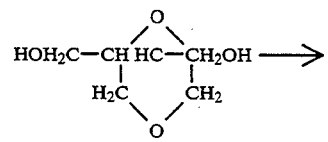

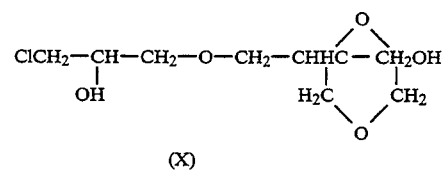
(X)

The product (X) may further undergo dehydrochlorination to yield a molecule with a terminal epoxy functionality. This epoxy functionality may then undergo further addition reactions with hydroxyl groups. The terminal hydroxyl functionality in (X) is also available for addition reactions with epoxy functionalities. Thus, repeating the addition-dehydrochlorination-addition reaction sequence may be expected to yield polyethercyclicpolyols of chemical composition represented by the formula given for Structure (V) (vide supra).

Alternatively, glycidol may be further hydrolyzed to glycerol, shown in Equation (9).

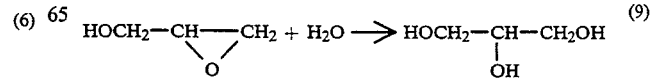

Further, glycidol, a difunctional epoxyalcohol, may also self-react to produce linear polyglycerol, as shown in Equations (10) and (11).

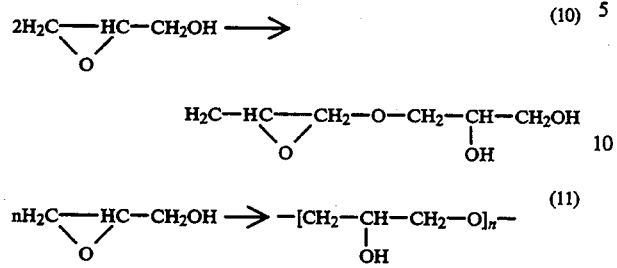

This reaction of glycidol with itself to form linear polyglycerols requires large concentrations of glycidol in the mixture, and thus it does not occur to a large extent under the usual reaction conditions (vide infra).

Polyhydric Alcohols

Polyhydric alcohols that are at least dihydric are required. The water solubility of the polyethercyclicpolyol product may depend on the polyol used, however. Thus, glycols, triols, tetrols, etc. are suitable reactants. Nonlimiting examples include ethylene glycol, diethylene glycol, triethylene glycol, tetraethylene glycol, polyethylene glycols, propylene glycol, butanediols, pentanediols, hexanediols, glycerol (which is the preferred polyol reactant), telomers of glycerol, such as diglycerols, triglycerols, tetraglycerols, pentaglycerols, and hexaglycerols, mixtures of glycerol and telomers of glycerol such as diglycerols and triglycerols, 1,5,6,9-decanetetriol; 1,2,4,5-cyclohexanetetramethanol; 1,2,4,7-heptanetetriol; 1,2,3,5-heptanetetriol; 4,4-dimethyl-1,2,3-pentanetriol; 1,3,4-cycloheptanetetriol; 1,2,3-pentanetriol; 1,2,4-pentanetriol; 2,3,4-pentanetriol; 1,1-cyclopentanediol; 1,2,3-cyclopentanetriol; 1,2,3-hexanetriol; 1,2,4-hexanetriol; 1,2,3,4-hexanetetriol; 1,2,4-cyclohexanetriol; 1,2,5-cyclohexanetriol, 1,2,3,4-cyclohexanetetriol; 1,2,3,5-cyclohexanetetriol; sorbitol, mannitol, 2,5- and 2,6-bis(hydroxymethyl)-p-dioxanes, copolymers of ethylene glycol and propylene glycols with the preceding alcohols, and mixtures of the preceding alcohols. An important class of polyhydric alcohols with straight carbon chains and four or more hydroxyl groups, called sugar alcohols, can also be used in preparing additive formulations containing cyclic polyethers. Sorbitol and mannitol are two such well-known polyhydric alcohols.

Precursors of trihydric polyols are also suitable reactants. For example, glycidol, an epoxy alcohol (vide supra) which upon reaction with water hydrolyzes to give glycerol, is an excellent reactant. Similarly, epoxy-1-butanol is also an excellent reactant. The preferred structure of polyol precursors is given by Structure (XI)

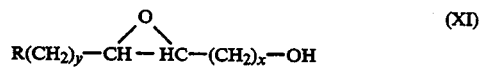

where R=H, OH, 1-12C alkyl, cycloalkyl, aryl, alkaryl, or aralkyl and x>1 and y>0, with the condition that when y=0, then R=H.

Derivatives of polyols are also useful feeds. For example, derivatives of glycerol, including linear and cyclic dimers, such as cis- or trans-2,5-bis(hydroxymethyl)-p-dioxane (XII), cis- or trans-2,6-bis(hydroxymethyl)-p-dioxane (XIII), and the glycerine acetal of hydracrylaldehyde (XIV) can react with epihalohydrins to produce polyethercyclicpolyols.

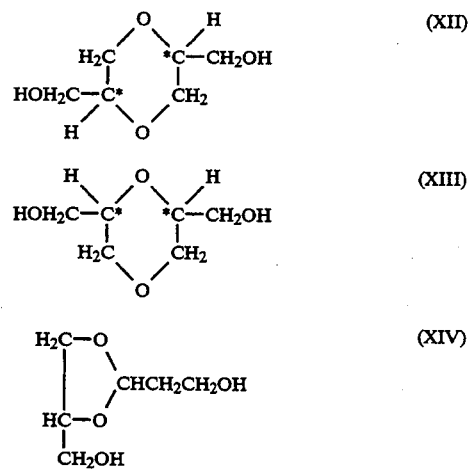

Known commercial mixtures of bis(hydroxymethyl)-p-dioxanes and polyols, especially glycerol, can react with epihalohydrins to produce polyethercyclicpolyols. Polyols, for example polyglycerols, are suitable reactants. Footstill bottoms (heavy ends from the manufacture of glycerol) are mixtures of glycerol, bis(hydroxymethyl)-p-dioxanes, linear polyglycerols, and small amounts of low molecular weight polyethercyclicpolyols, and are useful as a polyol reactant.

Byproducts or effluent streams from other existing processes for which the principal products are resins, soaps, and the like, can be excellent feedstocks. Exemplary are process streams of glycerol/glycidol mixtures which may contain other components, for example, mixtures of glycerol, glycidol, epichlorohydrin, dimethyl ketone, isopropyl alcohol, and/or sodium chloride made in the manufacture of resins. Such streams may first be processed to remove the nonglycerol-related material, for example, sodium chloride and/or water. Effluent streams from processes such as resin manufacture fit this category of feedstock. Such streams may contain predominantly water and salt (10 to 15 percent by weight), with small amounts of glycerol, glycidol, bis(hydroxymethyl)-p-dioxanes, and polyethercyclicpolyols of low molecular weight (and therefore initially ineffective for use in drilling fluids). For example, in an existing plant, the components of an effluent stream are 12 to 15 percent by weight sodium chloride, 0.3 to 2 percent by weight glycerol , 0.3 to 1.2 percent by weight glycidol, and less than 0.5 percent by weight polyglycerols, bis(hydroxymethyl)-p-dioxanes, and low molecular weight polyethercyclicpolyols, with the balance being water.

Epihalohydrins

Epihalohydrins are compounds which contain an epoxy group and a halogen in the vicinal position to the epoxy group. This is represented by Structure (xv).

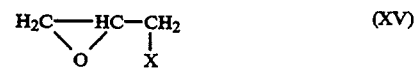

In general, any epihalohydrin, such as epichlorohydrin, epibromohydrin, epiiodohydrin, and epifluorohydrin, may be used in the preparation of polyethercyclicpolyols, and may substitute for epichlorohydrin in Equations (1)–(3). The preferred epihalohydrin is epichlorohydrin.

Alkali Metal or Alkaline Earth Metal Hydroxides

Alkali metal hydroxides have the general formula MOH, where M=Na, K, Li, Rb and Cs. Alkaline earth metal hydroxides have the general formula M'(OH)$_2$, where M'=Ca, Mg, Sr, Be, and Ba. In general, any alkali metal and/or alkaline earth metal hydroxide, such as sodium hydroxide, potassium hydroxide, lithium hydroxide, rubidium hydroxide, cesium hydroxide, calcium hydroxide, magnesium hydroxide, barium hydroxide, strontium hydroxide, or beryllium hydroxide, may be used in the preparation of polyethercyclicpolyols, and may substitute for sodium hydroxide in Equations (1)–(3). Preferably, sodium hydroxide, potassium hydroxide, lithium hydroxide, calcium hydroxide, or magnesium hydroxide is the metal hydroxide. Most preferably, sodium hydroxide or potassium hydroxide is the metal hydroxide.

Process Conditions

The preparation of polyethercyclicpolyols via thermal condensation of polyhydric alcohols has been described in patent applications Ser. Nos. 672,200; 672,199; 672,201; 672,198; 672,203 and 672,202 filed Mar. 19, 1991. In the thermal condensation reaction, a predetermined quantity of moles of water per mole of reactant are removed. In contrast, in the present invention, while water is a byproduct of the dehydrochlorination reaction (vide supra), no specific quantity of water need be removed from the reaction mixture. Instead, a specified molar ratio of epihalohydrin to polyol (vide infra) is preferred for the preparation of polyethercyclicpolyols. The thermal condensation reaction must be conducted at subatmospheric pressures to assist in removing the water of condensation. In the present invention, the reaction is typically carried out at atmospheric conditions, although reduced pressures may be used if desired. The onset of the thermal condensation reactions occur above 210° C. In contrast, the addition reactions described in the present invention occur at much lower temperatures, specifically 50° C. 200° C. In the thermal condensation, additional reactant is added as the degree of condensation increases, and the reaction is initially endothermic, becoming exothermic only as the reaction exceeds completion by removal of over 1.4 H$_2$O per mole of glycerol in the product. In the present invention, the epihalohydrin reactant (or alternatively the metal hydroxide reactant) is added slowly to control the reaction temperature since the addition-dehydrochlorination-addition reaction sequence is exothermic. Finally, in the thermal condensation, only polyols are used which have at least three hydroxyl groups of which are least two of the hydroxyl groups are vicinal. In contrast, in this present invention polyols which have at least two hydroxyl groups may be employed.

Seven variables appear to affect the molecular weight and cyclic content of the product polyethercyclicpolyols: 1) the concentration of epihalohydrin in the reaction mixture at a given time (or the epihalohydrin addition rate), 2) the molar epihalohydrin to polyol ratio, 3) the concentration of alkali and/or alkaline earth metal hydroxide in the reaction mixture, 4) the concentration of water in the reaction mixture at a given time. 5) solvent type and amount, 6) reaction temperature, and 7) reaction time.

Epihalohydrins are hazardous chemicals which must be handled with great care; special precautions and procedures were used in these preparations. The epihalohydrin is usually added to reaction mixtures slowly (either in a slow, continuous flow or portionwise) in order to control the reaction temperature, since the reaction of epihalohydrin with polyols is exothermic (as are most reactions of epihalohydrins). Besides controlling the temperature, the slow addition rate has the added benefit of regulating undesired side reactions which may increase in importance when the epihalohydrin concentration in the mixture is high. Alternatively, the metal hydroxide reagent may be added slowly to a mixture of polyol and epihalohydrin with similar results to that described above.

The epihalohydrin/polyol molar ratio employed varies with the nature of the polyol used. Normally an excess of epihalohydrin above the stoichiometric molar ratio of one predicted for a linear polymer of infinite length is preferred. This is because of the competing desired cyclization reaction and both the desired and undesired hydrolysis reactions described earlier. However, if a polyol reactant is employed which already has a moderate molecular weight and/or already contains some cyclic ether structures, for example, a low molecular weight polyethercyclicpolyol that one is trying to upgrade, or a byproduct stream which is composed of approximately 85 percent glycerol and 15 percent bis(-hydroxymethyl)-p-dioxanes, a molar epihalohydrin/-polyol ratio of less than one may be desired. Thus, an epihalohydrin/polyol molar ratio of 0.3–3.0 is preferred, with 0.70–2.0 being most preferred.

The reaction consumes metal hydroxide stoichiometrically with epihalohydrin; however, an excess of metal hydroxide is used in practice. A metal hydroxide/epihalohydrin molar ratio of 1.0–4.0 is preferred, with 1.05–1.55 being most preferred. Solid metal hydroxide is preferably used to control the concentration of water in the reaction mixture, although concentrated (e.g. 50% weight) aqueous solutions of metal hydroxide may also be used as the metal hydroxide source instead of the solid.

Solid metal hydroxide is generally added to the polyol at the beginning of the reaction. This addition is exothermic; reaction occurs between the metal hydroxide and the polyol to produce metal alkoxide and water. When the mixture is heated, the reaction is accelerated, especially if water is removed from the mixture. A thick, pasty white solid is formed. At least part of the polyol is likely converted to its alkali and/or alkaline earth metal salt.

The amount of water present at the beginning of the reaction has a large effect in a practical sense. With some polyols the reaction mixture becomes a concrete-like solid mass just after epihalohydrin addition is started, unless some water is added to the mixture. The solidification of the polyol/metal hydroxide mixture can also occur without any epihalohydrin addition by heating the mixture above 135° C. The fluidity of the mixture can be restored by adding a small amount of water. The water concentration in the mixture at any given time is a critical variable because of the various hydration reactions that can occur, leading to low molecular weight products. The effect of this variable may depend on other reaction variables, for example, the type and amount of solvent used or the epihalohydrin/-polyol ratio.

In principle, water added to the reactions can be minimized (in order to maximize the average molecular weight of the polyethercyclicpolyol) without sacrificing fluidity by using a solvent. The use of a solvent is, however, optional; polyethercyclicpolyols may be prepared without the use of a solvent. Acetone is the preferred solvent. Other solvents, including ketones, ethers and hydrocarbons, such as methyl ethyl ketone, toluene and diglyme may also be used. Alcohols, especially mono-alcohols, will react with the epoxy alcohol in addition reactions, and thus alcohols are not suitable solvents. Similarly, compounds containing other functional groups, such as amines, which are reactive with epoxy groups, are not useful as solvents for the reaction. The weight ratio of solvent/polyol used is preferably 0.05-20, and is most preferably 0.5-10. Acetone is not a good solvent for the metal hydroxide/polyol mixture in the absence of water; the reaction mixture is inhomogeneous. In this inhomogeneous mixture, reaction to form polyethercyclicpolyols will still occur. The mixture with acetone can be made homogeneous, however, by the addition of small amounts of water.

The use of a solvent such as acetone may also increase the cyclic content of polyethercyclicpolyols. In these reactions, the polyol/metal hydroxide is only slightly soluble in the acetone, and the resulting mixture is a two-phase mixture. It is theorized, although the invention is not limited to this theory, that inhomogeneity of the mixture promotes the formation of cyclic bis(hydroxymethyl)-p-dioxane units, since the epihalohydrin is soluble in the acetone phase, which appears to contain little of the metal hydroxide/polyol mixture. This may enhance the occurrence of cyclization reactions.

The reaction temperature varies with the solvent that is chosen. If acetone is used as the solvent, the mixture will initially reflux at or near 58° C., with the temperature of reflux increasing gradually as the reaction occurs. The temperature range is preferably 50° C.-200° C., most preferably 58° C.-150° C. Condensate from the vapor may be returned to the reaction mixture, or a portion of it may be withdrawn. The condensate is typically a mixture of water (formed in the dehydrochlorination reaction), epihalohydrin and solvent, if solvent is used. The reaction is generally conducted under atmospheric conditions, although it may be conducted under reduced pressure if desired.

The reaction time has been found to be a significant reaction variable; sufficient time must be allowed for all the epihalohydrin to react. Preferably, the desired reaction temperature is maintained for 10-300 minutes after epihalohydrin addition is complete, and most preferably for 20-180 minutes. Incomplete reaction may be evidenced directly by analysis of the reaction mixture for unreacted epihalohydrin, or indirectly by the requirement of an excess of acid above that theoretically required to neutralize the metal hydroxide remaining after reaction.

Part of the metal halide salt byproduct may also be removed by precipitation through the addition of a lower alkanol, such as n-propanol, methanol, n-butanol or n-pentanol. As the average molecular weight of the polyethercyclicpolyol samples increases, however, this salt extraction becomes less feasible; much of the product may precipitate with the solid salt.

A typical polyethercyclicpolyol preparation is carried out as follows: a 500 ml 4-neck resin kettle is fitted with a thermocouple, a nitrogen inlet, a metering addition funnel, an air-driven stirrer and a condenser (optionally fitted with a distillation head for solvent recovery). Preparations are optionally conducted under a low nitrogen flow at atmospheric pressure. The reactions may also optionally be run under reduced pressure to facilitate removal of water from the system.

Polyalcohol (for example, glycerol), solvent (if used, preferably acetone) and metal hydroxide (preferably sodium or potassium hydroxide) are added to the flask. The mixture is stirred and heated. The reaction temperature is preferably 50° C.-200° C., and is most preferably 55° C. -160° C. The reaction temperature depends on the solvent used. When acetone is the solvent, the reaction temperature is held lower by the acetone refluxing. When no solvent is used, the mixture temperature can easily rise above 140° C. The specific effect of reaction temperature on the product molecular weight and composition is unknown.

After the mixture reaches the desired reaction temperature, epihalohydrin (preferably epichlorohydrin) is then added dropwise from the addition funnel. Temperature control is achieved via evaporative cooling. Condensate water may be withdrawn or recycled to the flask. It may be necessary to add water as required to maintain a fluid mixture especially if water is removed from the reaction as it is formed. The mixture is stirred at least 90 minutes after the epihalohydrin addition is complete. Concentrated mineral acid, preferably hydrochloric, phosphoric or sulfuric acid, is added to neutralize the excess metal hydroxide and/or adjust the mixture pH to a desired value. The amount of acid used may be calculated from the excess of metal hydroxide employed. Low boiling solvent, if used, is then distilled from the mixture. Some of the water added to or formed in the reaction may also be removed by distilling under reduced pressure at this point.

If removal of part of the salt byproduct is desired, a lower alkanol, preferably methanol, n-propanol, n-butanol or n-pentanol, is added to the warm mixture with stirring. The mixture is removed from the flask and centrifuged at 3500 rpm for 45 minutes. (Alternatively, the precipitated salt may be removed by filtration.) The centrifuged mixture often comprises two or three layers. When there are three layers, the top layer contains mostly n-alkanol and light ends, the middle layer is mostly polyethercyclicpolyol and the bottom layer is mostly salt. The middle layer is then evaporated at >120° C. and 20 mm Hg until no more water or solvent are removed.

The sample is typically diluted with water to 50 percent by weight for use as a drilling fluid additive. The sample may be analyzed for Cl$^-$ content. FAB-MS may be used to evaluate cyclic components (vide infra). $^{13}$C NMR may also provide evidence of cyclicity (vide infra). Liquid and/or gas chromatography may be used to analyze light ends.

The appearance of the 50 percent weight aqueous samples varies widely. Some samples have a translucent jelly-like appearance, some are white or deep yellow rubbery solids, and some are liquid. Some of the samples appear to retain much of the acetone solvent, as evidenced by the small amount of solvent recovered on distillation and by the distinctive odor. This acetone left in the samples could not be removed by rotary evaporation at 140° C. and 20 mm Hg pressure. It is theorized, though the invention is not limited to this theory, that the different preparations may contain different amounts of cross-linking, and that the highly crosslinked samples may absorb the acetone solvent very strongly.

A concentrated effluent stream that came from a resins plant has been employed as the polyol in order to increase its molecular weight. These preparations are made in a similar manner to that described above.

Characterization and Analysis

It was disclosed earlier in patent applications Serial Nos. 672,203; 672,202; 672,200; 672,199; 672,201 and 672,198 filed Mar. 19, 1991 that there is a strong relationship between the weight average molecular weight ($M_w$) and the performance of polyethercyclicpolyols as drilling fluid additives.

Molecular weights referred to in these patent applications were determined using a three-column gel permeation chromatographic (GPC) technique using three Ultrahydrogel columns: a Linear column, a 250 angstrom column, and a 120 angstrom column in series, using water solvent at 30° C. Using this technique, polyethercyclicpolyols produced by the methods described in the above cited patent applications range from $M_w$ values of 20,000 to 300,000. Preferred polyethercyclicpolyols in the above cited patent applications have $M_w$ values in the range of 50,000 to 200,000.

However, the GPC chromatograms for polyethercyclicpolyols show a complex dependence upon the concentration of metal halides, such as sodium chloride. Therefore, the GPC-based molecular weights measured for the polyethercyclicpolyols obtained by the addition of epihalohydrin to polyol in the presence of alkali or alkaline earth metal hydroxide may be affected by the large and varying concentrations of alkali and/or alkaline earth metal halide byproduct contained in the samples. Thus, no GPC determination of $M_w$ values is reported for polyethercyclicpolyols produced in the present invention.

Fast atom bombardment mass spectrometry (FAB-MS) and C-13 nuclear magnetic resonance spectroscopy (NMR) techniques have been used to characterize polyethercyclicpolyol samples. FIG. 1 shows a comparison of the fast atom bombardment mass spectra of a) a concentrate of an aqueous effluent stream containing glycerol and its precursors, b) a polyethercyclicpolyol prepared via the thermal polycondensation of the glycerol concentrate described in a), as disclosed in the earlier patent application Ser. No. 672,200 filed Mar. 19, 1991, and c) a polyethercyclicpolyol prepared via the addition of epichlorohydrin and glycerol in the presence of sodium hydroxide, as described in Example 2 (vide supra).

The glycerol concentrate in FIG. 1A shows prominent ions at m/z 115 and 137, corresponding to the ionization of glycerol via attachment of one and two sodium atoms, respectively. Therefore, ionization via sodium adduction is expected for the hydroxyl-containing components in the samples. A series of masses m/z 189, 263, 337, etc. (symbolized by ◯) is also observed. Each member of this series is separated by 74 mass units, consistent with the addition of one glycerol unit (molecular weight 92) with the expulsion of one molecule of water (molecular weight 18). The molecular weights of the sodiated ions in this series are consistent with the (linear) condensation products of glycerol. In the presence of sodium, it is common to observe the replacement of acidic hydrogens with sodium, thus increasing the mass of the ion by 22. This series is represented in FIG. 1A by the symbol ∇.

Figure 1B:
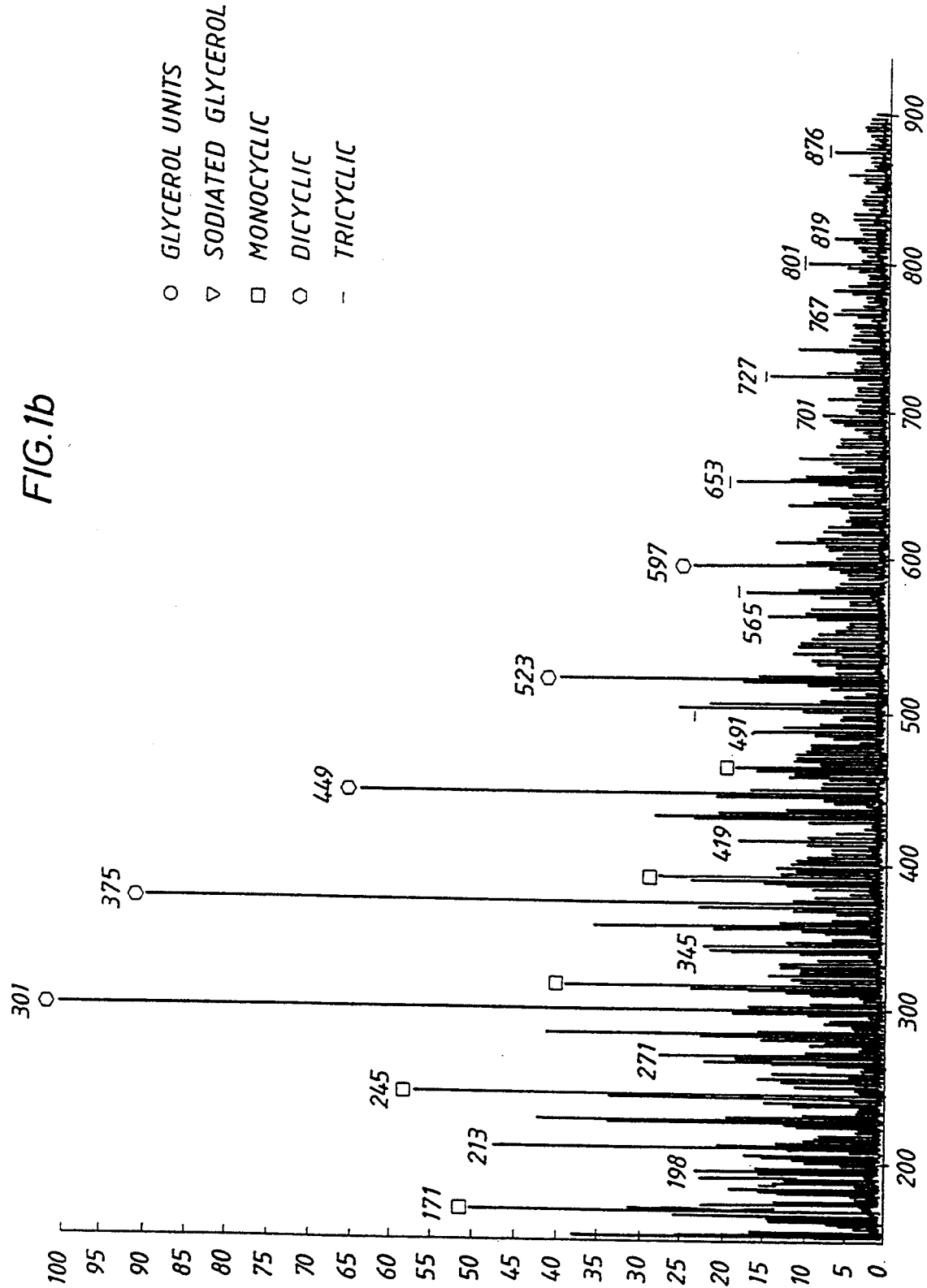
Figure 1C:
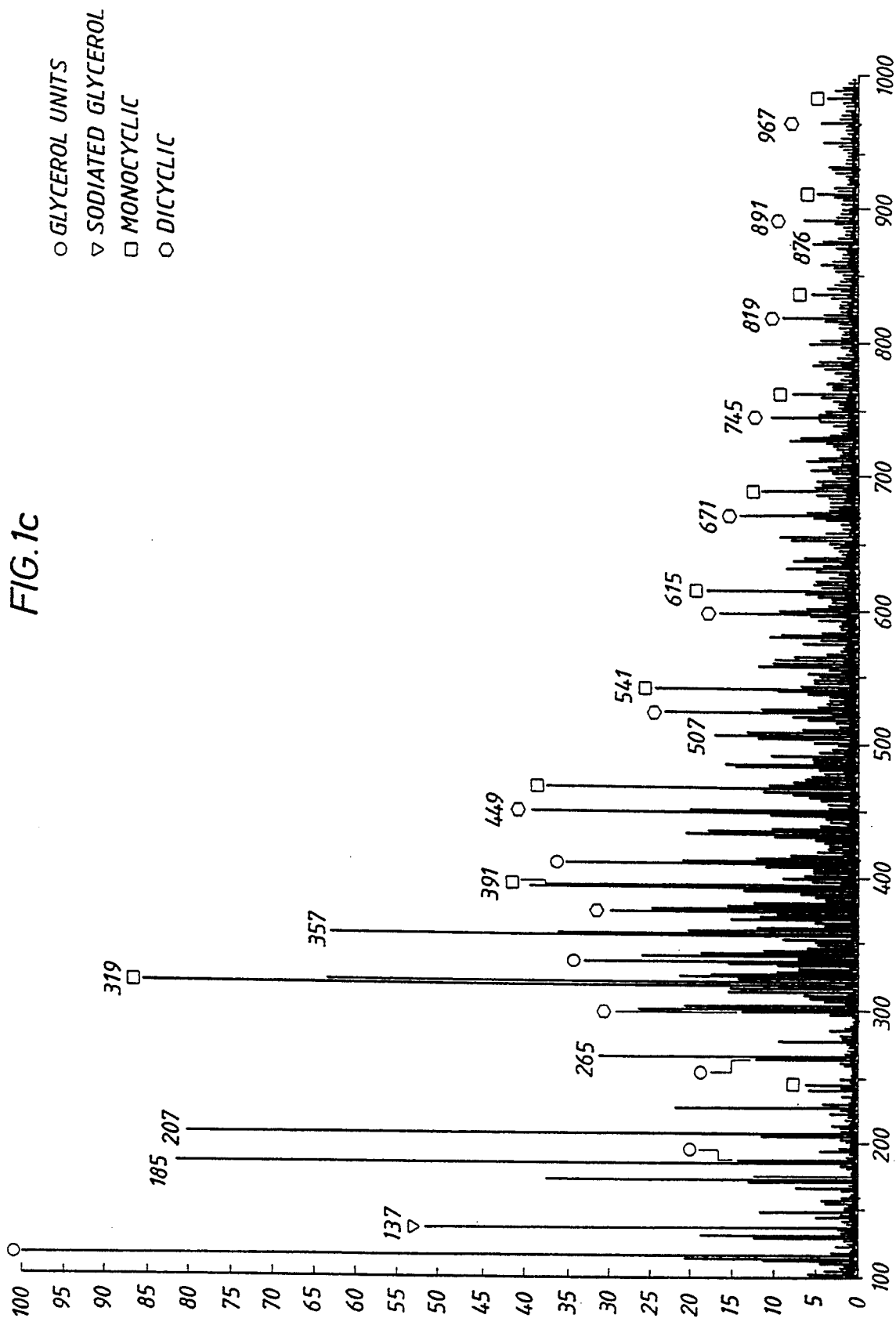

Note that the above series of ions, ◯ and ∇, are not abundant in the polyethercyclicpolyol samples in FIG. 1B and 1C. However, a loss of water from the condensation product of glycerol results in the series represented by

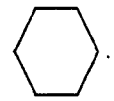.

It is expected that with the additional loss of one molecule of water, the glycerol dimer will form the six-membered ring diether structure, bis(hydroxymethyl)-p-dioxane. This series, based on the monocyclic dimer was observed in both the glycerol concentrate (FIG. 1A) and the polyethercylicpolyol samples (FIGS. 1B and 1C).

The condensation of four glycerol units, producing a 12-carbon-containing oligomer, presents the first opportunity for the formation of a dicyclic compound, through yet another loss of water. The series represented by and beginning at m/z 301 is consistent with the expulsion of water from the monocyclic tetramer at m/z 319 to produce the dicyclic tetramer. This series, based on the dicyclic tetramer, was observed in all the samples, however, the dicylic species dominate the spectrum of the polyethercyclicpolyol in FIG. 1B and are abundant in the spectrum of FIG. 1C.

The opportunity to increase the number of 6-membered rings in the polymer chain presents itself with each addition of two glycerol units, that is six carbons. Therefore, the dicyclic hexamer of glycerol (18 carbons, m/z 449) would form the tricyclic hexamer m/z 431, with the loss of water. The series of ions indicating the presence of the tricyclic hexamer does not appear in the spectrum of the glycerol concentrate in FIG. 1A, yet this higher mass series, symbolized by—, indicating the tricyclic hexamer is prominent in the polyethercyclicpolyol sample in FIG. 1B. This series of ions does not appear in the polyethercyclicpolyol sample in FIG. 1C.

The high molecular weight series of ions beginning with the tricyclic hexamer is observed for as many as 12 glycerol units, m/z 876, however detection limitations cause higher mass components to become increasingly more difficult to ionize and detect by this method.

Therefore, it may be seen from the FAB-MS spectra that the aqueous effluent stream concentrate (shown in FIG. 1A) contains some cyclic glycerol-derived products along with linear polyglycerols, however, the polyethercyclicpolyols represented in FIGS. 1B) and 1C), prepared by the thermal condensation of polyols and by the addition of epihalohydrins and polyols as described herein, respectively, show that the linear polyglycerol is not abundant and the sample consists mostly of the cyclic glycerol-derived products.

Figure 2A:
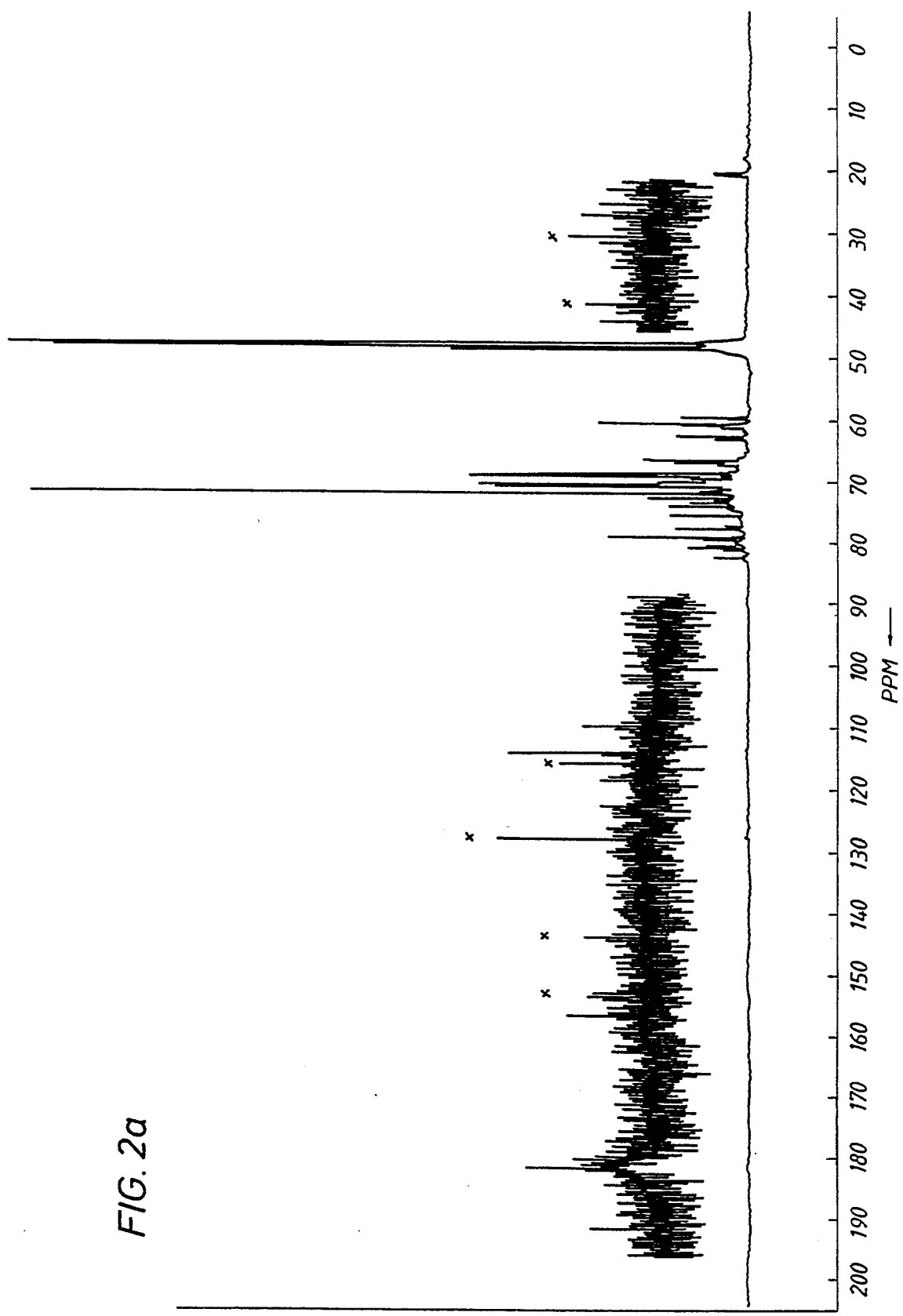
FIGS. 2A–2C disclose nuclear magnetic resonance spectroscopy for various samples.
Figure 2B:
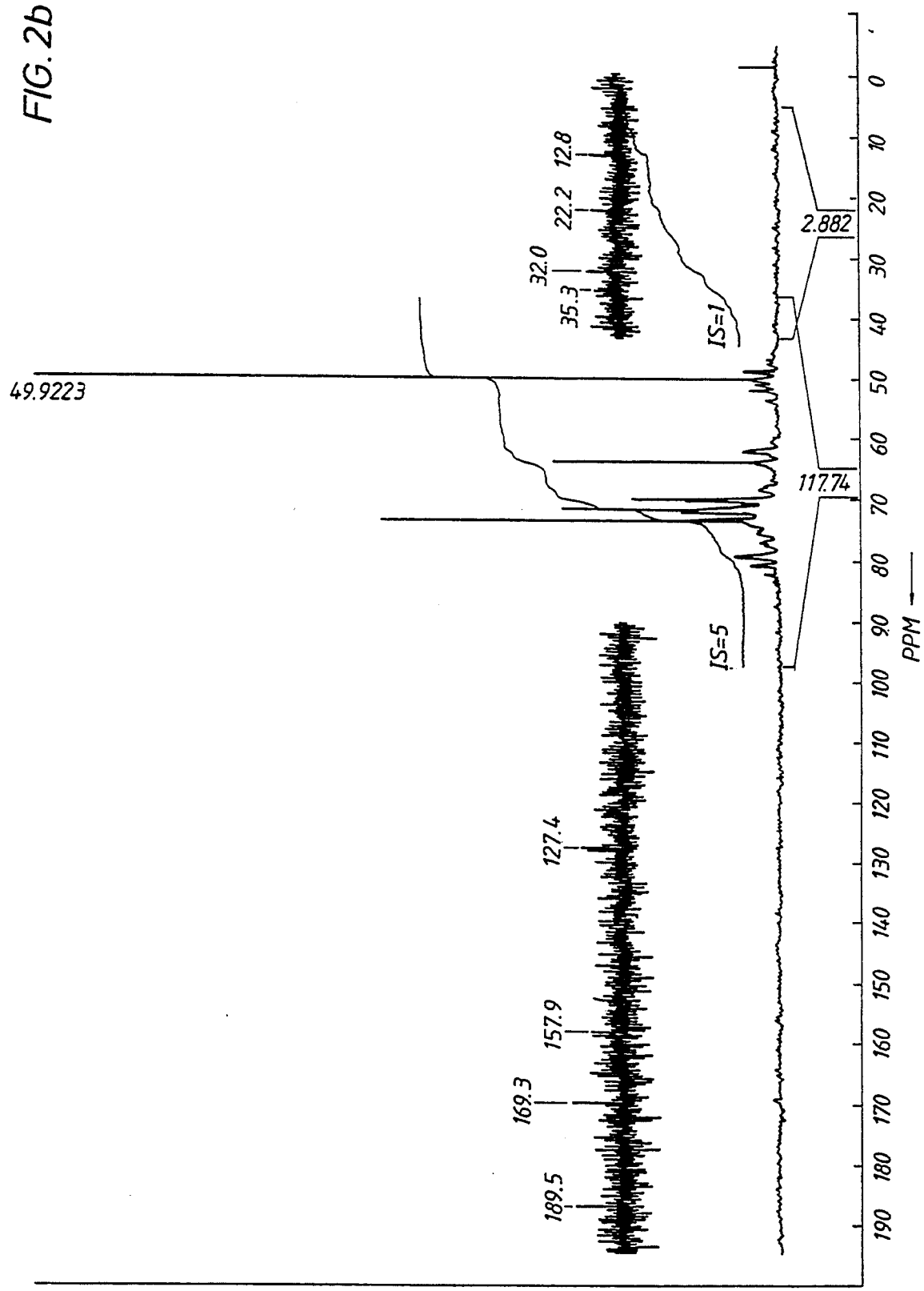
Figure 2C:
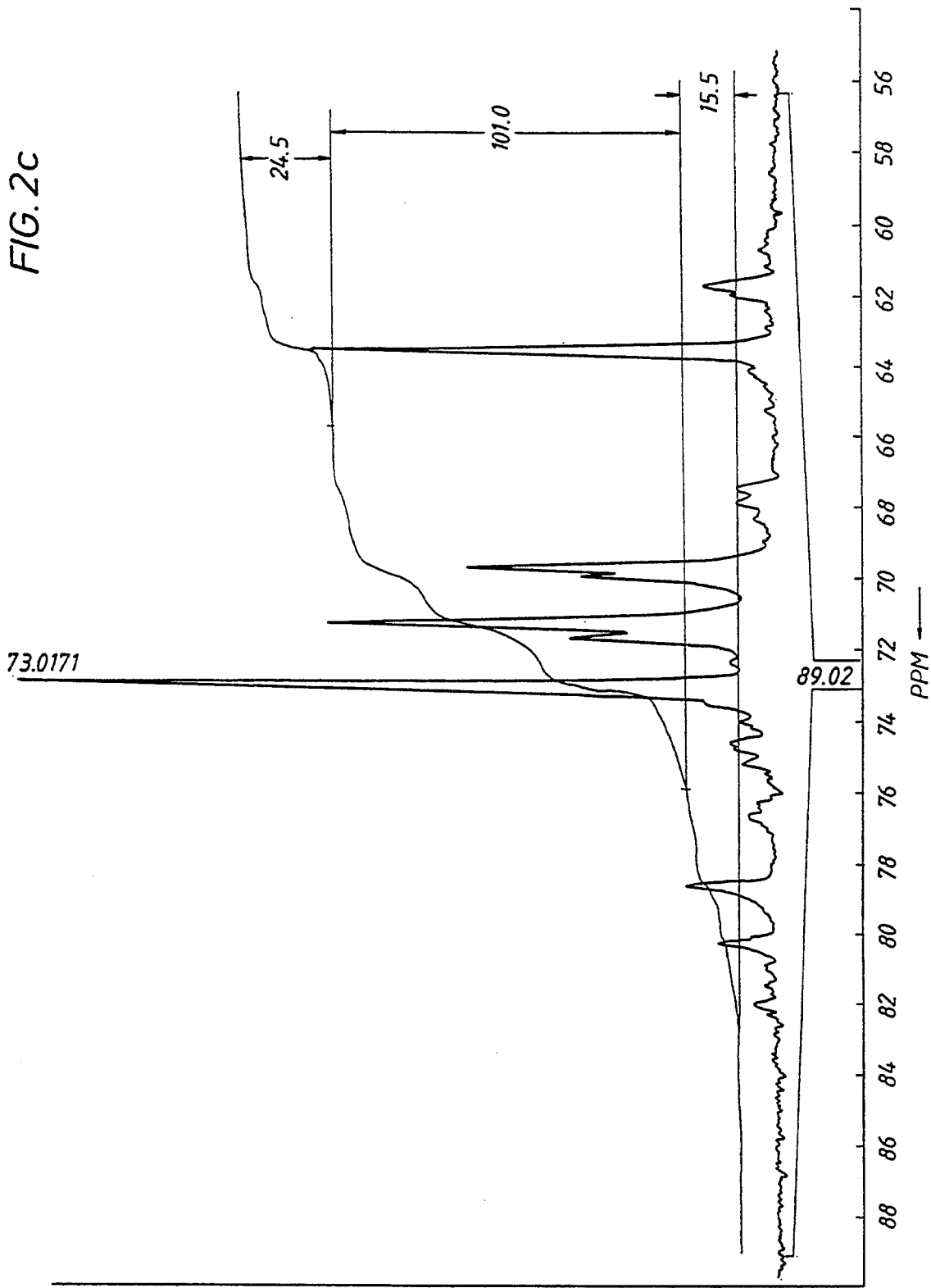

C-13 NMR analysis of the polyethercyclicpolyol samples dissolved in methanol or D₂O/methanol are shown in FIG. 2. FIG. 2 shows a comparison of the C-13 NMR spectra of a) a polyethercyclicpolyol prepared via the thermal polycondensation of the glycerol concentrate described above, as disclosed in the earlier patent application Ser. No. 672,200 filed Mar. 19, 1991, and b) a polyethercyclicpolyol prepared via the addition of epichlorohydrin and glycerol in the presence of sodium hydroxide. The NMR spectra show similar chemical structure and are consistent with the structures proposed for these samples. The components of interest occur in the C-13 NMR spectrum between 90 and 55 ppm chemical shift. This part of the spectrum can be broken down into three regions:

90–76 ppm: Branch point/cyclization point carbons RR'CH—OR"
Internal linear carbons —CH$_2$—OR
65–55 ppm: Linear terminal carbons —CH$_2$—OH The integrals of the peaks in these three regions of the C-13 NMR spectrum for the samples shown in FIG. 2 are summarized in Table 1.

TABLE 1

| Sample | 90–76 ppm Integral | 76–66 ppm Integral | 66–55 ppm Integral | Sum | Branches Per 100 Polymerized C$_3$ Units | Ends Per 100 Polymerized C$_3$ Units |
|---|---|---|---|---|---|---|
| FIG. 2A | 20 | 103.5 | 15 | 138.5 | 43 | 32 |
| FIG. 2B | 15.5 | 101 | 24.5 | 141 | 33 | 52 |

Since the polyethercyclicpolyol is of an unknown high molecular weight, the integrals of the three regions cannot be used to differentiate between an average molecular structure and an average repeat unit structure. What can be stated, however, is that for the polyethercyclicpolyol sample prepared via thermal polycondensation (FIG. 2A), the branch point/cyclization point carbons outnumber the terminal carbons. Such a situation cannot be reconciled with a structure that is simply branched and therefore the structure must be at least partially cyclized. The C-13 spectrum of the sample prepared via addition of epichlorohydrin and glycerol (FIG. 2B) is similar to the thermally prepared sample, but has lower cyclicity.

Since the FAB-MS profiles shown in FIGS. 1B) and 1C) are similar, showing the presence of both monocyclic and dicyclic species in FIG. 1C), we conclude that polyethercyclicpolyols may be produced by the method of the present invention described herein. This conclusion is further supported by the C-13 NMR data.

EXAMPLES

Example 1

Preparation of Polyethercyclicpolyol Via Addition of Epichlorohydrin and Glycerol in the Presence of Sodium Hydroxide 204 g glycerol (2.21 moles) and 128 g granular solid sodium Ehydroxide (3.20 moles) were charged to a 500 ml resin kettle fitted with a thermocouple, a nitrogen inlet, a metering addition funnel, an air-driven stirrer and a condenser cooled with room temperature water. A nitrogen flow of 5 standard cubic feet per hour (SCFH) was begun. A heating mantle was used to heat the kettle. The mixture was heated to 110° C. The temperature was held at 110° C. for 10 minutes. This portion of the heating was carefully controlled as the reaction is exothermic. Vapor was observed rising from the mixture after the temperature reached 108° C. After 10 minutes, the nitrogen flow was reduced to 1.5 SCFH. 172 ml epichlorohydrin (203g, 2.20 moles) was then added dropwise from the addition funnel over a period of 93 minutes, for an average addition rate of 1.8 ml/min. The reaction temperature was maintained between 110° C. and 113° C., during which time the mixture refluxed. All reflux was returned to the reaction mixture. Water was added to the mixture as follows: 5 ml at 28 minutes after the epichlorohydrin addition was begun, 1 ml at 95 minutes, 1 ml at 96 minutes, 2 ml at 97 minutes, 1 ml at 98 minutes, 2 ml at 99 minutes, 3 ml at 100 minutes, 5 ml at 102 minutes, 5 ml at 104 minutes, and 5 ml at 105 minutes, for a total of 30 ml water added. Heating was continued for 17 minutes after the epichlorohydrin addition was complete. At this point, 376 ml of deionized water was added to the mixture, which was then neutralized with 105 ml (126 g, 1.28 moles) of 37% weight aqueous hydrochloric acid to a pH of 7. The pH of the final sample was 7. The product was a gray opaque liquid. 550 g of product were obtained. A substantial amount (120 g) of white solid material remained in the mixture after stirring well. This solid was not readily soluble in water. It was removed by centrifugation. Analysis of the final mixture showed 52% weight water.

Example 2

Preparation of Polyethercyclicpolyol Via Addition of Epichlorohydrin and Glycerol in the Presence of Sodium Hydroxide, Employing Acetone as the Solvent 203 g glycerol (2.20 moles), 129 g granular solid sodium hydroxide (3.22 moles), and 350 mL acetone were charged to the apparatus described in Example 1. A nitrogen flow of 5 SCFH was begun. The mixture was heated to 58° C. and was allowed to boil for 15 minutes. 172 ml (203 g, 2.20 moles) epichlorohydrin was added dropwise over 80 minutes, for an average addition rate of 2.2 ml/min. Three minutes after the epichlorohydrin addition was started, an additional 150 ml acetone was added to the mixture. Five minutes after the epichlorohydrin addition was started, the nitrogen flow was reduced to 1.5 SCFH. The reaction temperature was maintained between 60° C. and 70° C., during which time the mixture refluxed. Heating was continued for 40 minutes after the epichlorohydrin addition was complete. At this point, the mixture climbed up the stirring shaft, and 25 ml of deionized water was added to dilute the mixture. The mixture was then neutralized with 82 ml (98.4 g, 1.0 mole) of 37% weight aqueous hydrochloric acid. The pH of the mixture was then adjusted to 11 with a small amount of 50% weight aqueous sodium hydroxide. Finally, 475 ml of deionized water was then added to the solution. The yellow product had a jelly-like consistency. Analysis of the final mixture showed 50% weight water and 9.9% weight Cl$^-$. As a drilling fluid additive, the sample showed good performance in fluid loss reduction, and excellent performance in swelling reduction and cuttings dispersion reduction.

Example 3

Preparation of Polyethercyclicpolyol Via Addition of Epichlorohydrin and Glycerol in the Presence of Sodium Hydroxide, With Salt Removal 116 g glycerol (1.25 moles) and 72 g solid sodium hydroxide pellets (1.8 moles) were charged to the apparatus described in Example 1. A nitrogen flow of 2 SCFH was begun. The mixture was heated to 97° C. and dropwise addition of 98 ml epichlorohydrin (116 g, 1.25 moles) was begun. The epichlorohydrin was added over 37 minutes, for an average addition rate of 2.6 ml/min. The nitrogen flow was not reduced. 5 ml deionized water was added to the mixture 5 minutes after the epichlorohydrin addition was begun. All reflux was returned to the mixture. The mixture was diluted with 15 ml of deionized water. A portion of the salt by-product was then removed from the resulting mixture. The mixture was first neutralized with 38 ml (55 g, 0.56 mole) of 85% weight aqueous phosphoric acid (55 g, 0.56 moles). The resulting mixture was then stirred. 200 ml n-propanol was then added to the mixture, with stirring. The resulting mixture was then centrifuged at 50°–70° C. and 3500 rpm for 45 minutes. After centrifuging, the sample separated into 3 layers. The middle layer was stripped of volatiles in a rotary evaporator at 159° C. until no more distillate was removed. The sample was then diluted with deionized water to 50 percent by weight. 315 g of a very pale yellow, viscous liquid were obtained. Analysis of this sample showed 2.2% weight Cl−. As a drilling fluid additive, the sample showed good performance in fluid loss reduction.

Example 4

Preparation of Polyethercyclicpolyol Via Addition of Epichlorohydrin and a Mixture of Glycerol and Bis(Hydroxymethyl)-p-dioxane in the Presence of Sodium Hydroxide, With Salt Removal 116 g of a commercially available mixture of bis(hydroxymethyl)-p-dioxanes and glycerol and 72 g solid sodium hydroxide pellets (1.8 moles) were charged to the apparatus described in Example 1, except that a distillation head allowing for complete or partial take off of reflux was attached to the apparatus between the resin kettle and the condenser, and that chilled (11° C.) water was used to cool the condenser. A nitrogen flow of 2 SCFH was begun. The mixture was heated to 105° C. and dropwise addition of 98 ml epichlorohydrin (116 g, 1.25 moles) was begun. The nitrogen flow was not reduced. The mixture temperature was maintained around 110° C. during the epichlorohydrin addition. The condensate separated into two layers. The heavier phase containing mostly epichlorohydrin was returned to the mixture; 46 ml of the lighter phase containing mostly water was removed. 60 ml deionized water was added to the mixture in 10 portions during the epichlorohydrin addition: 5 ml at 30 minutes, 5 ml at 38 minutes, 5 ml at 50 minutes, 5 ml at 54 minutes, 10 ml at 60 minutes, 10 ml at 65 minutes, 5 ml at 67 minutes, 5 ml at 72 minutes, 5 ml at 75 minutes, and 5 ml at 84 minutes. The mixture was allowed to stir at 120° C. after the epichlorohydrin addition was complete. The mixture was diluted with 15 ml of deionized water. A portion of the salt byproduct was then removed from the resulting mixture. The mixture was first neutralized with 38 ml (55 g, 0.56 mole) of 85% weight aqueous phosphoric acid (55 g, 0.56 moles). The resulting mixture was then stirred and then temperature brought back up to 120° C. 15 ml condensate (mostly water) was removed from the mixture. 200 ml n-propanol was then added to the mixture, with stirring. The resulting mixture was then centrifuged warm at 3500 rpm for 45 minutes. After centrifuging, the sample separated into 3 layers: a clear, colorless liquid on top, an opaque white jelly and a white, grainy, wet solid. The middle layer was stripped of volatiles in a rotary evaporator at 120° C. until no more distillate was removed. The sample was then diluted with deionized water to 50 percent by weight. Analysis of this sample showed 1.8% weight Cl−. As a drilling fluid additive, the sample showed good performance in fluid loss reduction.

Example 5

Preparation of Polyethercyclicpolyol Via Addition of Epichlorohydrin and Glycerol in the Presence of Sodium Hydroxide in Acetone Solvent, With Salt Removal 92 ml glycerol (116 g, 1.3 moles), 72 g solid sodium hydroxide pellets (1.8 moles) and 200 ml acetone were charged to the apparatus described in Example 1, except that a 500 ml 4-neck round bottom flask was used instead of a resin kettle. A nitrogen flow of 2 SCFH was begun. The mixture was heated to 58° C. and dropwise addition of 98 ml epichlorohydrin (116 g, 1.3 moles) was begun. The nitrogen flow was not reduced. The temperature rose to 66° C. and was held there as the mixture refluxed. When about half of the epichlorohydrin had been added, 20 ml water was added to the mixture. The mixture was held at 61° C. for 15 minutes after the epichlorohydrin addition was complete. The material climbed the stirring shaft. 20 ml additional water was added to the mixture to dilute it. The mixture was neutralized with 38 ml (55 g, 0.56 mole) of 85% weight aqueous phosphoric acid. Part of the salt byproduct was then removed from the mixture by adding 200 ml n-propanol with stirring, followed by centrifuging the warm mixture at 3500 rpm for 45 minutes. After centrifuging, the sample had separated into 3 layers, a clear, yellow liquid, a white gelatinous solid and a white, grainy, wet solid. The middle gelatinous layer was stripped of volatiles on a rotary evaporator at 80° C. for 1 hour. This sample was diluted to 50% by weight with deionized water. 488 g of a clear jelly-like semi-solid was obtained. Analysis of this sample showed 4.5% weight Cl−. As a drilling fluid additive, the sample showed good performance in fluid loss reduction, and good performance in swelling reduction and cuttings dispersion reduction.

Example 6

Preparation of Polyethercyclicpolyol Via Addition of Epichlorohydrin and Aqueous Glycerol Effluent Concentrate in the Presence of Sodium Hydroxide in Acetone Solvent, With Salt Removal 161 g of a aqueous resins plant effluent concentrate mixture containing glycerol and its precursors, 36 g solid sodium hydroxide pellets (0.9 moles), and 200 ml acetone were charged to the apparatus described in Example 1, except that chilled (11° C.) water was used to cool the condenser. A nitrogen flow of 2 SCFH was begun. The mixture was heated to reflux (58° C.) and dropwise addition of 49 ml epichlorohydrin (58 g, 0.63 moles) was begun. The nitrogen flow was not reduced. The mixture temperature was maintained around 63° C. during the epichlorohydrin addition. The epichlorohydrin was added over 21 minutes, for an average addition rate of 2.3 ml/min. The mixture was allowed to stir at 62° C. for 30 minutes after the epichlorohydrin addition was complete. A portion of the salt byproduct was then removed from the resulting mixture. The mixture was first neutralized with 19 ml (28 g, 0.28 mole) of 85% weight aqueous phosphoric acid. The resulting mixture was then stirred and then 200 ml n-propanol was then added to the mixture. Acetone (about 200 ml) was distilled from the sample. The resulting mixture was then centrifuged warm at 3500 rpm for 45 minutes. After centrifuging, the sample separated into 2 layers. The top layer was stripped of volatiles in a rotary evaporator at 120° C. until no more distillate was removed. The sample was then diluted with deionized water to 50 percent by weight. Analysis of this sample showed 1.6% weight Cl−. As a drilling fluid additive, the sample showed good performance in fluid loss reduction.

Example 7

Preparation of Polyethercyclicpolyol Via Addition of Epichlorohydrin and Glycerol in the Presence of Sodium Hydroxide in Methyl Ethyl Ketone Solvent, With Salt Removal 116 g glycerol (1.3 moles), 72 g solid sodium hydroxide pellets (1.8 moles) and 200 ml methyl ethyl ketone were charged to the apparatus described in Example 1, except that chilled (11° C.) water was used to cool the condenser. A nitrogen flow of 2 SCFH was begun. The mixture was heated to 78° C. for 10 minutes, and dropwise addition of 98 ml epichlorohydrin (116 g, 1.3 moles) was begun. The nitrogen flow was not reduced. The temperature was held between 78° C. and 88° C. as the mixture refluxed. The epichlorohydrin was added over 78 minutes, for an average addition rate of 1.3 ml/min. The mixture was held at about 80° C. for 25 minutes after the epichlorohydrin addition was complete. The mixture was neutralized with 81 ml (97 g, 0.99 mole) of 37% weight aqueous hydrochloric acid to a pH of 5.5. Part of the salt byproduct was then removed from the mixture by adding 200 ml methanol with stirring, followed by centrifuging the warm mixture at 3500 rpm for 45 minutes. After centrifuging, the sample had separated into 2 layers, a liquid and a white, grainy, wet solid. The liquid layer was stripped of volatiles on a rotary evaporator at 187° C. for 1.75 hours. This sample was diluted to 50% by weight with deionized water. 220 g of liquid product was obtained.

What is claimed is:

1. A method for preparing polyethercyclicpolyols, comprising:

a) heating a reaction mixture comprising an alkali and/or alkaline earth metal hydroxide with a reactant selected from the group consisting of (1) a polyol having at least two hydroxyl groups, (2) precursors of the polyol, (3) cyclic derivatives of the polyol, and (4) mixtures thereof;
   b) admixing epihalohydrin with the reaction mixture at a temperature between 50° C. and 200° C. to initiate an addition reaction between the epihalohydrin and the reactant, the admixed quantity of epihalohydrin being such that the epihalohydrin/reactant molar ration is 0.3–3.0; and
   c) continuing heating the reaction mixture until the reaction goes substantially to completion to form a product mixture.

2. The method of claim 1 wherein the reactant and the metal hydroxide are first mixed with a solvent and then heated.

3. The method of claim 1 wherein water is present in the reaction mixture after admixing with said epihalohydrin, and said water is at least partially removed.

4. The method of claim 1 wherein water is present in the reaction mixture and, prior to admixing said epihalohydrin, said water is at least partially removed.

5. The method of claim 1 wherein a lower alkanol is added to the product mixture to precipitate a salt and the salt is removed from the product mixture.

6. The method of claim 1 wherein the epihalohydrin/reactant molar ratio is 0.7–2.0.

7. The method of claim 1 wherein the metal hydroxide/epihalohydrin molar ratio is 1.0–4.0.

8. The method of claim 1 wherein the metal hydroxide/epihalohydrin molar ratio is 1.05–1.55.

9. The method of claim 1 wherein solid metal hydroxide is added to the reactant at the beginning of the addition reaction.

10. The method of claim 1 wherein the epihalohydrin/reactant molar ratio is 0.7–2.0 and the metal hydroxide/epihalohydrin molar ratio is 1.05–1.55.

* * * * *